United States Patent [19]

Subrini

[11] Patent Number: 5,788,627
[45] Date of Patent: Aug. 4, 1998

[54] CAVERNOSAL EXTENSION IMPLANTS

[76] Inventor: Louis Subrini, Domaine de la Batallie, 5 Rue Emmanuel Chabrier, 78370 Plaisir, France

[21] Appl. No.: 569,014

[22] Filed: Dec. 7, 1995

[51] Int. Cl.⁶ .................................................. A61F 5/00
[52] U.S. Cl. ............................ 600/40; 600/38; 600/39
[58] Field of Search ............................ 600/38, 39, 40; 623/11

[56] References Cited

U.S. PATENT DOCUMENTS

| 4,411,055 | 10/1983 | Simpson et al. | 29/447 |
| 4,532,920 | 8/1985 | Finney | 600/40 |
| 5,063,914 | 11/1991 | Cowen. | |
| 5,067,485 | 11/1991 | Cowen. | |
| 5,088,477 | 2/1992 | Subrini | 600/40 |
| 5,376,064 | 12/1994 | Cerny | 600/38 |

FOREIGN PATENT DOCUMENTS

| 0320203 | 6/1989 | European Pat. Off. |
| 0430788 | 6/1991 | European Pat. Off. |
| 0526016 | 2/1993 | European Pat. Off. |
| 80/00302 | 3/1980 | WIPO |

*Primary Examiner*—Jennifer Bahr
*Assistant Examiner*—Rosiland Kearney
*Attorney, Agent, or Firm*—Larson & Taylor

[57] ABSTRACT

A penile implant to irreversibly and definitively lengthen the corpus cavernosum by using the tissue expansion phenomenon. The implant includes a pressure chamber, a pressure regulator for regulating the pressure in the pressure chamber, an irreversibly extensible device, and a body of synthetic material of a predetermined length and covered with a tip. The device is used to permanently lengthen the male penis.

20 Claims, 1 Drawing Sheet

CAVERNOSAL EXTENSION IMPLANTS

BACKGROUND OF THE INVENTION

1. Field of the Invention

The present invention concerns a cavernosum extension implant, whose goal is to importantly and definitively lengthen the corpus cavernosum, by using tissue expansion, in order to obtain an irreversible lengthening.

2. Description of the Prior Art

The tissue expansion is a physiological phenomenon by which any tissue submitted to a tension, lengthens until there is no tension. The phenomenon is reproducible, any new tension entailing a new lengthening. In the present invention the goal being to lengthen the penis, one will research a tissue expansion of corpus cavernosum in the longitudinal direction.

The disadvantage of available penile implants even those that can lengthen by whatever mechanism, is that they are unable to lengthen the corpus cavernosum. They are not in fact designed for this goal, but solely to allow penetration to impotent patients, by giving to the penis an artificial rigidity.

All available penile implants inert or inflatable, have at rest a constant length. The concern to obtain a longer penis during erection than at rest, has behaved to design prostheses whose length can be adapted using a bellows or an analogous system. During flaccidity, prostheses are at their minimum length. When the patient desires an erection, he activates a system of pump, what entails an increase of the rigidity of prostheses, then a certain degree of lengthening until the prostheses occupy all the available length of the corpus cavernosum. After intercourse, the patient de-activates the system, and then the prostheses loose their rigidity and come back to their initial length.

The disadvantage of such systems is that the difference of prosthesis length between the two conditions of flaccidity and rigidity is limited, about 2 centimeters approximately. An other disadvantage is that this lengthening is reversible and temporary, being produced only in erection, and therefore unable to induce a tissue expansion of corpus cavernosum, which needs a continuous pressure. On the other hand, the lengthening of prostheses entails their stiffening which is in fact the researched goal.

Others penile erection prostheses comprise a device for adjustment of their length, in order to adapt as precisely as possible the length of the prosthesis to that of the corpus cavernosum. The shortening or the lengthening of the prosthesis is obtained by injection or by withdrawal of a fluid into a bellows, according to whether the prosthesis is too long or too short for the corpus cavernosum where it is inserted. But the device can be lengthened only to the extent of the length of the corpus cavernosum which allows it, and in any case of negligible manner.

Globally, disadvantages of these systems, are that they are designed to rigidify the penis during the penetration by means of a limited and reversible lengthening. They obtain no lengthening of the corpus cavernosum, function for which they are not designed.

An other disadvantage of these devices is due to the fact that the lengthening of prostheses habitually is using bellows, or more precisely undulations whose thickness is constant. Any cavity whose wall is of a constant thickness and whose internal pressure increases, tends to take a spherical shape. Thus such a device that comprises folds withdrawn on themselves in shape of bellows, when submitted to an increase of pressure, will have tendency not only to be lengthened by unfolding of the bellows, but also to be enlarged by increase of its transverse diameter. A part of energy is therefore used to increase the diameter instead of to be entirely available to entail an extension of the system in a preferential direction, which is direction of the lengthening, that is the sought-after goal by the present invention.

An other disadvantage of this shape is that each envelope is of a little height, so that the lengthening of the system, even entirely unfolded is poor, unless to multiply the number of folds, what the length of the corpus cavernosum allows as much less than the penis is short.

Some patients, impotent or not, present a short penis, that necessitates to lengthen the corpus cavernosum not temporary during erection, but on the contrary definitively, so as to give to the penis a normal length, what the present invention plans to realize.

The goal is to lengthen the corpus cavernosum using an implant including a device for extension, which using an external source of fluid can be lengthen gradually up 6 to 10 centimeters, without obligatory increasing its transverse diameter.

SUMMARY OF THE INVENTION

The penile implant according to a first characteristic, is an elongated body, preferably with a circular cross-section such that represented in FIG. 1.

It includes: the body of the implant 7, a spherical-conical shaped chamber of pressure, with a cavity that constitutes a site for injection, and that communicates through an anti-return valve with the extension device. The corpus of the implant 7 is made from a synthetic material preferably homogeneous whose hardness is included between 20 and 50 shore A approximately. It is intended to be tailor cut to the desired length, then possibly covered by a tip 10 whose extremity is identical or analogous to that of the opposite extremity. At the moment of insertion, each device has a length such that it occupies all the available length of the corpus cavernosum where it is inserted. Each tip of the device being located in the corresponding cul-de-sac of each corpus cavernosum.

A chamber of pressure that constitutes a site of injection of fluid, communicates by the intermediary of a valve with a sheath in which slides the body of the implant. The addition of fluid by an injection into the chamber, using a little needle increases its internal pressure, pushes the body of the implant and lengthens the whole device, inducing so a lengthwise tissue expansion of the corpus cavernosum. The more the pressure of injection and the injected volume are important, the more the speed of the expansion tissue is high. As soon as the lengthening of the corpus cavernosum has reached a certain degree, the injection has to be renewed, inducing again a new cavernous tissue extension. Injections are repeated until to obtain the penile lengthening desired.

A pressure regulator using a simple system is connected to the syringe, in order to allow adjunction of fluid into the chamber, only below an adjustable and predetermined threshold of pressure, in order to avoid any over-pressure in the device.

According to not restrictive modes of realization:

The extensible segment of the device may be accordion shaped, composed by a piling of several little height cylinders, realizing so hollow discs which are connected together.

The extensible segment of the device can be constituted by a system of spring inserted when in compressed shape, which will lengthen gradually by using its own energy.

The addition of fluid can be made using a system of pump connected to the device.

The chamber of pressure, the regulator, and the pump may be separated or located outside of the corpus cavernosum and separated from the body of the implant. They may be connected by one or more appropriate tubes, realizing thus an implant of two or more parts.

BRIEF DESCRIPTION OF THE DRAWINGS

Annexed drawings illustrate the invention.

The FIG. 1 represents a cross-section of the device according to the invention where the extensible segment is composed by the body of the implant sliding in a sheath.

Figure 2:
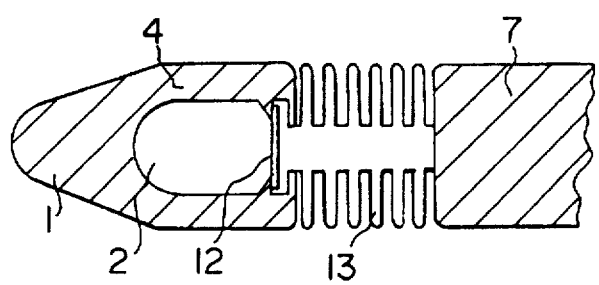

The FIG. 2 represents a variant of the device, where the extensible segment is composed by a hollow disc piling.

Figure 3:
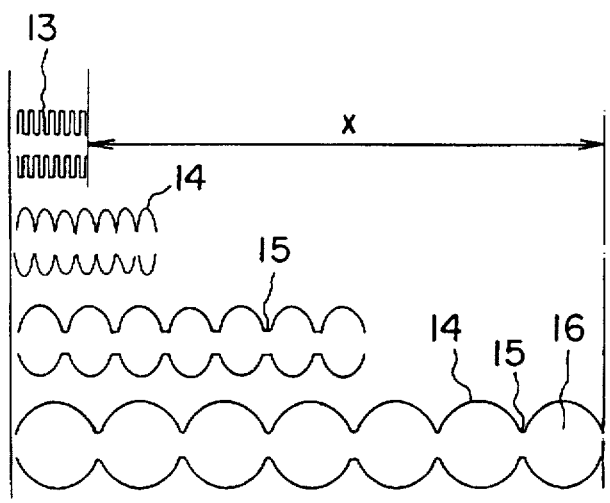

The FIG. 3 illustrates the result obtained by the increase of the internal pressure in the hollow discs.

Figure 4:
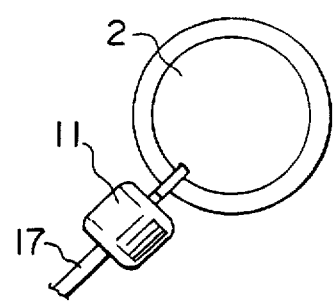
Figure 4:
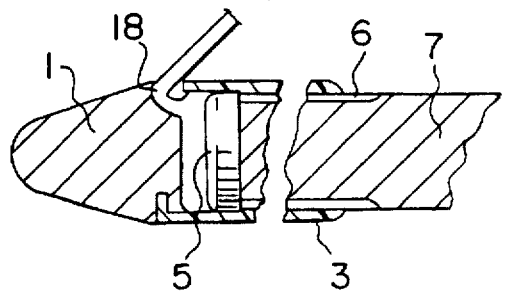

The FIG. 4 represents a cross-section in a variant of the device, where the chamber and the regulator of pressure are separated from the body of the implant.

DETAILED DESCRIPTION OF THE PREFERRED EMBODIMENT

Figure 1:
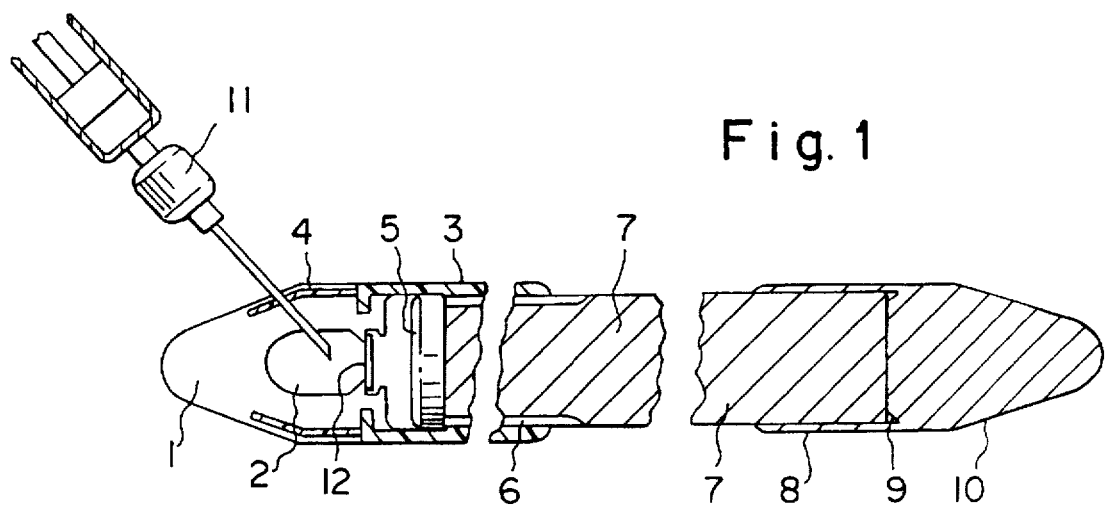

In reference to these drawings, a extension penile implant, according to a first characteristic, presents with an elliptic or circular cross section, as represented in the FIG. 1. The extremity 1 is either rounded or spherical-conical, in order to be well adapted to the internal anatomy of the corpus cavernosum cul-de-sac. The opposite extremity of the device is to be cut at the desired length, then covered with a tip 10 of a similar or identical shape to that of the extremity 1.

The device of extension comprises a chamber of pressure 2 and a sheath 3, in which slides the body of the implant 7. The wall of the chamber of pressure is made from a bio-compatible material, and may be if necessary reinforced by a sheath 4 for example using Dacron, in order to resist to the increase of pressure and to allow several injections, without any fluid leak through the hole created by the needle.

According to one of the modes of the invention, the chamber of pressure 2 may include a resistant valve 12, for example metallic in order to prevent fluid to come back from the extensible segment to the chamber. Thus even in the case of a leak through the pressure chamber wall, the extensible part of the device keeps its internal pressure. Additionally, the valve realizes a shield preventing the needle to penetrate into the extensible part.

The sheath 3 is of a little thickness, such that its external diameter is the closest possible to that of the body of the implant, to provide a quasi constant external diameter. The sheath presents an internal area adapted to the corpus of the implant in order to insure the tightness of the system. Its length authorizes a motion of the implant body of about approximately 8 centimeters.

The body of the implant is preferably of a cylindrical cross section. Its extremity can be reinforced by a piston 5, or by in a hollow cylinder 6. The implant can be connected to the piston, for example by sealing, unless the surgeon inserts it into the hollow cylinder. In that case it is possible if necessary, to shorten the body of the implant before its introduction into the cylinder 6, by a transverse section using a scalpel blade. The body of the implant is made from silicone or from any bio-compatible material. According to one of the modes of the invention, this material may present a weak resistance to the axial compression, which allows the body of the implant to amortize effects of a not desired excess of pressure. According to one of the modes of the invention, as a not restrictive example, a such amortized system is insured for example by an silicone elastomer, that under the effect of an axial compression of 500 grams undergoes a deformation that shortens a cylindrical implant corpus of 12 mm of diameter, by about 2 to 6%, and for a length of 15 cm a shortening of about 6 mm. Such a function may be insured for example by an silicone elastomer the hardness of which is approximately about 20 to 50 shore A. The tip 10 is rounded, or preferably spherical-conical and continues with a flange 8. It may be made from a material, analogous to that of the body of the implant. Once the body of the implant 7 has been cut to the desired length, it is covered with the tip whose shape is well adapted to the cavernosum cul-de-sac that has to receive it. The tip may advantageously comprise one or several cavities, for example a peripheral throat 9 such that repelling the flange on the implant, will empty all or a part of the cavity and to entail thus an effect of suction, able to resist to the wrench of the tip.

During its installation, the totality of the cavernosum extension implant is of a total length such that it occupies the entire available length of the corpus cavernosum where it is inserted.

The direct puncture of the chamber 2 through the skin and through the wall of the corpus cavernosum, using a fine needle connected to a syringe, allows injection of fluid, for example normal saline into the chamber. So, internal pressure increases and repels the body of the implant thus lengthening the device.

A regulator of pressure 11 may be inserted between the syringe and the needle, in order not to allow any delivery of fluid into the chamber, if its inner pressure is higher than an adjustable or predetermined threshold. Thus any overpressure in the device is avoided. The pressure on the two opposite extremities of the corpus cavernosum provokes a longitudinal tissue expansion of the corpus cavernosum that lengthens gradually. According to one of the modes of the invention, once the corpus cavernosum lengthening has reached a certain degree, the injection is renewed as many times as necessary, any injection inducing a new cavernosum tissue expansion, until the penis desired length is obtained. The frequency and the volume of injections is obviously variable according to the pathology, the rapidity and the importance of the lengthening desired. It can be slow, for example with the rhythm of an injection of 1 milliliter all 20 days, or on the contrary rapid with an unique and continuous injection, for a duration of about one hour, as much as allowed by the adjustment of the regulator of pressure, and the elasticity of the corpus cavernosum.

Penile extension implants are inserted either definitively or temporary. In this last case, they are removed when the desired lengthening has been obtained, and may possibly be replaced by definitive penile implants.

According to an other modality of the invention, the system is lengthen by the use of its own energy. Such a device can be realized in one of its applications for example by a system of spring, not represented, that is inserted in its compressed shape and in contact with the body of the implant, and that progressively lengthens the device.

According to one of the modes of the invention, the extensible segment is composed of a piling of several little height cylinders, realizing so hollow discs 13, the totality appearing with the shape of an accordion, such that illustrated by the FIG. 2. Cavities of the discs communicate at the level of the axis of discs, and are filled with a fluid, for example normal saline. Before insertion, each face of the hollow discs 13, is joined to the adjacent faces, and is separated only by a virtual space or quasi virtual. This is only for the legibility of figures, that discs are represented separated by a space. Each disc wall is made from a bio-compatible material, for example silicone, whose hardness is preferably about 35 shore A, this example being not restrictive. According to one of the modes of the invention, each fold 14 located on disc circumference, as well as each fold 15 located at the union between two neighbor discs is more resistant than are the faces of discs, either because a greatest thickness (not represented) or because a whatever strengthening. Thus, when a new quantity of fluid is added to the device, the volume of each disk is increased until to become spherical without tendency to increase in diameter, as illustrated on the FIG. 3. The maximum lengthening x permits by the device is function of the number and of the diameter of discs, the diameter of the axial cavity, and the face thickness of discs.

According to one of the modes of the invention, as illustrated by the FIG. 3, the device is constituted from seven discs, each face with a thickness of 0.5 mm, a diameter of 12 mm, and whose axial cavity diameter is 2.5 mm. Such a device has a total lengthening capacity of seven centimeters approximately, each addition of 1 ml of fluid providing a lengthening of about 1 cm of the device. Figures above are given as an example, and it is permissible to modify one or several of these parameters according to needs. According to an other mode, in order to avoid the increase of diameter and to guide the lengthening by limiting its flexion capacities, the totality of the accordion can be located in a sheath not represented, that could be analogous to the sheath 3 of FIG. 1.

The modes of the invention above describe an en-bloc system, where all constitutive elements of the device of extension are integrated in a totality, excepted the regulator of pressure which is external to the system.

According to one of the modes of the invention, such that illustrated by the FIG. 4, the chamber of pressure 2, and the regulator of pressure 11 are separated from the body of the implant and the extensible device, and realize thus a two-parts device connected by a tube 17 that transmits the fluid by a connection 18 to the lumen of the sheath 3. In that case, if at an appropriate volume and at a sufficient pressure, the pressure chamber may be filled only once, without necessitating repeated injections. So, in proportion as the corpus cavernosum is lengthened by tissue expansion, the internal pressure of the extensible segment decreases, and the regulator allows then a new passage of fluid to the extensible segment, which recovers its initial internal pressure and entails a new tissue expansion. The device is so working with a quasi constant pressure and automatically.

To avoid the multiplication of figures, only an example of realization is represented in FIG. 4, but the various elements of the system will be able to be distributed differently, and situated in a different location in the implant according to needs. In such a two-parts or several parts system, addition of fluid can be made by injection into the chamber 2, or according to an other mode of the invention, by pressure on a small pump (not represented) that by an appropriate connection system allows the addition of fluid to the extensible segment, without any injection.

At the opposite, according to one of the modes of the invention not illustrated, all of the parts of the device including the regulator of pressure and the pump, may be integrated in the corpus of the implant, without any external connection tube.

Applications of the invention are all the conditions where it is necessary to obtain a definitive and important lengthening of the penis. Main indications are represented by penile atrophy pathologies either congenital, as for example micropenis, microphallus and epispadias, either acquired, as cavernosum fibrosis of Peyronie's disease.

I claim:

1. Penile implant to irreversibly and definitively lengthen the corpus cavernosum by using the tissue expansion phenomenon, comprising a pressure chamber, a pressure regulator connected to the pressure chamber to regulate the pressure in the pressure chamber, an irreversibly extensible device connected to the pressure chamber by an anti-return valve, said anti-return valve permitting passage of fluid from the pressure chamber to the irreversibly extensible device and preventing passage of fluid from the irreversibly extensible device to the pressure chamber, and a body of synthetic material of a predetermined, desired length covered with a tip which is connected to or forms a part of the irreversibly extensible device.

2. A penile implant in accordance with claim 1, wherein the tip includes a portion which is spherical-conical in shape, a flange, and one or more cavities designed to create a depression by a glass-cupping effect.

3. A penile implant in accordance with claim 2 wherein one or more parts of the implant are separated from the body of the implant in order to realize a two or more part penile implant.

4. An implant in accordance with claim 2, wherein the extensible segment comprises hollow disks which are in fluid communication with each other by a perforation at their center.

5. A penile implant in accordance with claim 2, wherein the extensible segment is constituted by the body of the implant sliding in a sheath.

6. A penile implant according to claim 2, wherein all of the elements of the implant are integrated into the body of the implant.

7. A penile implant in accordance with claim 1, further comprising a syringe and a needle associated with the syringe for injecting fluid into the pressure chamber and an adjustable pressure regulator located between the syringe and the needle for injecting fluid into the pressure chamber to prevent delivery of fluid to the pressure chamber if a pressure in the pressure chamber exceeds a predetermined threshold, wherein the pressure chamber is of a spherical-conical external shape and wherein the pressure chamber has an outer wall which is reinforced by a resisting sheath.

8. A penile implant in accordance with claim 7 wherein one or more parts of the implant are separated from the body of the implant in order to realize a two or more part penile implant.

9. A penile implant in accordance with claim 7, wherein the extensible segment is constituted by the body of the implant sliding in a sheath.

10. An implant in accordance with claim 7, wherein the extensible segment comprises hollow disks which are in fluid communication with each other by a perforation at their center.

11. A penile implant according to claim 7, wherein all of the elements of the implant are integrated into the body of the implant.

12. A penile implant in accordance with claim 1, wherein the extensible segment is constituted by the body of the implant sliding in a sheath.

13. An implant in accordance with claim 12, wherein the extensible segment comprises hollow disks which are in fluid communication with each other by a perforation at their center.

14. A penile implant according to claim 12, wherein all of the elements of the implant are integrated into the body of the implant.

15. A penile implant in accordance with claim 12 wherein one or more parts of the implant are separated from the body of the implant in order to realize a two or more part penile implant.

16. An implant in accordance with claim 1, wherein the extensible segment comprises hollow disks which are in fluid communication with each other by a perforation at their center.

17. A penile implant according to claim 16, wherein all of the elements of the implant are integrated into the body of the implant.

18. A penile implant in accordance with claim 16 wherein one or more parts of the implant are separated from the body of the implant in order to realize a two or more part penile implant.

19. A penile implant according to claim 1, wherein all of the elements of the implant are integrated into the body of the implant.

20. A penile implant in accordance with claim 1 wherein one or more parts of the implant are separated from the body of the implant in order to realize a two or more part penile implant.

* * * * *